(12) United States Patent
Pachot et al.

(10) Patent No.: US 8,436,192 B2
(45) Date of Patent: May 7, 2013

(54) 2-AMINO-2-PHENYL-ALKANOL DERIVATIVES, PREPARATION THEREOF, AND PHARMACEUTICAL COMPOSITIONS CONTAINING SAME

(75) Inventors: Jean Pachot, La Varenne Saint Hilaire (FR); Christophe Dini, Le Plessis Pate (FR)

(73) Assignee: Oraxcell, Romainville (FR)

( * ) Notice: Subject to any disclaimer, the term of this patent is extended or adjusted under 35 U.S.C. 154(b) by 0 days.

(21) Appl. No.: 13/387,462

(22) PCT Filed: Jul. 28, 2010

(86) PCT No.: PCT/FR2010/051598
§ 371 (c)(1),
(2), (4) Date: Jan. 27, 2012

(87) PCT Pub. No.: WO2011/012810
PCT Pub. Date: Feb. 3, 2011

(65) Prior Publication Data
US 2012/0129909 A1 May 24, 2012

(30) Foreign Application Priority Data
Jul. 30, 2009 (FR) .................................... 09 03750

(51) Int. Cl.
*C07D 207/02* (2006.01)
*A61K 31/40* (2006.01)
(52) U.S. Cl.
USPC .......................................... 548/570; 514/428
(58) Field of Classification Search .................. 548/570; 514/428
See application file for complete search history.

(56) References Cited

U.S. PATENT DOCUMENTS

| 5,326,878 | A | 7/1994 | Depernet et al. |
| 5,455,238 | A | 10/1995 | Aszodi et al. |
| 5,883,248 | A | 3/1999 | Aszodi et al. |
| 6,353,024 | B1 | 3/2002 | Grouhel et al. |
| 2009/0197924 | A1 | 8/2009 | Pachot et al. |

FOREIGN PATENT DOCUMENTS

| CA | 2407697 | 11/2001 |
| EP | 0 628 562 | 12/1994 |
| FR | 2 684 994 | 6/1993 |
| FR | 2 765 218 | 12/1998 |
| GB | 1 434 826 | 5/1976 |
| WO | WO 99/01417 | 1/1999 |
| WO | WO 2007/140611 | 12/2007 |

OTHER PUBLICATIONS

Martin, Arnaud et al.; "Synthesis of Methylamino-2-Phenyl-2-Butyl-3,4,5-Trimethoxybenzoate, The Main Bioactive Metabolite Of Trimebutine Maleate;" Arzneimittel-Forschung, 50(I), No. 6, XP-001538217, 2000; pp. 544-549.
Fiaux, Hélène et al.; "Pyrrolidine Derivatives As New Inhibitors of ∝—Mannosidases and Growth Inhibitors of Human Cancer Cells;" Laureates: Awards and Honors SCS Fall Meeting 2005, and Chimia 60, No. 4, 2006; XP-002478240 and XP-002478241; 7 pages.
Langlois, Annik et al.; "Fedotoxine Blocks Hypersensitive Visceral Pain In Conscious Rats: Action At Peripheral κ-Opioid Receptors;" European Journal of Pharmacology, 324, 1997; pp. 211-217.
Wheeler-Aceto Helen et al.; "Standardization of the Rat Paw Formalin Test For The Evaluation Of Analgesics;" Psychopharmacology, 104, 1991; pp. 35-44.
Brown, George B. "[3]H-Batrachotoxinin-A Benzoate Binding to Voltage-Sensitive Sodium Channels: Inhibition by the Channel Blockers Tetrodotoxin and Saxitoxin;" The Journal of Neuroscience, vol. 6, No. 7, Jul. 1986; pp. 2064-2070.

*Primary Examiner* — Robert Havlin
(74) *Attorney, Agent, or Firm* — Harness, Dickey & Pierce, P.L.C.

(57) ABSTRACT

Ester derivatives of 2-amino-2-phenyl-alkanol of general formula (I) in which: $R_1$ forms with $R_3$ and the nitrogen and carbon atoms to which they are respectively attached, a heterocycle with 4 to 7 members, optionally substituted in the α position of the nitrogen atom by one or two $R_a$ and $R_b$ radicals being able to be independently of one another hydrogen or linear or branched alkyl (1 to 4C), and $R_2$ is H or a —CO—O—$CHR_4$—$OCOR_5$ radical for which $R_4$ is H or linear or branched alkyl (1 to 4C), and $R_5$ is alkyl optionally substituted by benzyloxycarbonylamino, acylamino or by the remainder of an amino acid, or represents a heterocycle, or $R_2$ is linear or branched alkyl (1 to 4C), alkyl (2 to 4C) substituted by OH, alkoxy, alkylthio, $NH_2$, alkylamino, dialkylamino optionally forming with the nitrogen atom to which they are attached, a heterocycle with 5 or 6 members, it being understood that the substituted alkyl radical is linear or branched and comprises at least 2C between >N—$R_2$ and the substituent, unless specified otherwise, alkyl or acyl are linear or branched (1 to 7C), in their R or S forms or their mixtures, as well as its pharmaceutically acceptable salts, if any.

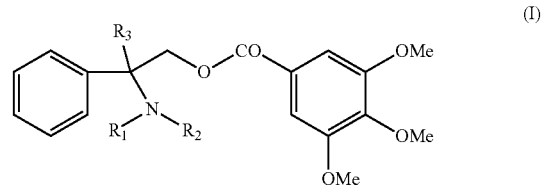

(I)

6 Claims, No Drawings

2-AMINO-2-PHENYL-ALKANOL DERIVATIVES, PREPARATION THEREOF, AND PHARMACEUTICAL COMPOSITIONS CONTAINING SAME

CROSS-REFERENCE TO RELATED APPLICATIONS

This application is a National Phase Entry of International Application No. PCT/FR2010/051598, filed on Jul. 28, 2010, which claims priority to French Patent Application Serial No. 0903750, filed on Jul. 30, 2009, both of which are incorporated by reference herein.

BACKGROUND AND SUMMARY

The present invention relates to 2-amino-2-phenyl-alkanol derivatives which are substituted in different ways and which are specially interesting, particularly for their analgesic action. The present invention also relates to the preparation of these derivatives as well as the pharmaceutical compositions comprising them.

In the International application WO 99/01417, (S) 2-methylamino-2-phenyl)butyl 3,4,5-trimethoxy benzoate and its use in the treatment of chronic pain has been described. In the European application EP 1 110 549, the use of trimebutine [(2-methylamino-2-phenyl)butyl 3,4,5-trimethoxybenzoate maleate] or its stereoisomers in the treatment of the inflammatory disorders and pain has been described.

In the British patent application GB 1 434 826, esters of amino alcohols of structure:

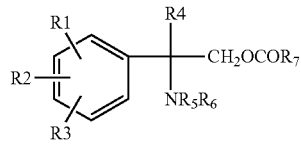

have been described in which R1 to R3 can be in particular a hydrogen atom, R4 can be an alkyl radical, R7 can be aryl optionally substituted by 1 to 3 alkoxy radicals and R5 and R6 represent a hydrogen atom, an alkyl or aralkyl radical or together form, with the nitrogen atom to which they are attached, a heterocycle. The products are useful as anti-spasmodic agents. The British application also describes carbamates for which $R_7$ has the structure —NH—R"$_7$. The aryl carbamates thus constituted possess an analgesic and anti-inflammatory activity. However, the modifications introduced on the amine are quite limited and are not able to lead to powerful analgesics.

DETAILED DESCRIPTION

It has now been found that the ester derivatives of 2-amino-2-phenyl-alkanol of general formula:

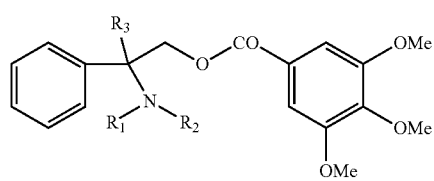

in which:

$R_1$ forms with $R_3$ and the nitrogen and carbon atoms to which they are respectively attached, a heterocycle containing 4 to 7 members, optionally substituted in the α position of the nitrogen atom, by one or two $R_a$ and $R_b$ radicals which can be independently of the other, a hydrogen atom or a linear or branched alkyl containing 1 to 4 carbon atoms, and $R_2$ is a hydrogen atom or represents a —CO—O—CHR$_4$—OCOR$_5$ radical for which $R_4$ is a hydrogen atom or a linear or branched alkyl radical containing 1 to 4C, and $R_5$ is an alkyl radical optionally substituted by benzyloxycarbonylamino, acylamino or by the remainder of an amino acid, or represents a heterocyclyl radical or $R_2$ represents an alkyl radical in a linear or branched chain containing 1 to 4C, an alkyl radical containing 2 to 4C substituted by hydroxy, alkoxy, alkylthio, amino, alkylamino, dialkylamino, the alkyl parts of which can form with the nitrogen atom to which they are attached, a heterocycle having 5 or 6 members, it being understood that said substituted 2 to 4C alkyl radical is in a linear or branched chain and comprises at least 2 carbon atoms between the nitrogen atom bearing $R_2$ and the substituent;

in their R or S forms or their mixtures, as well as their pharmaceutically acceptable salts, if any, have a specially interesting activity as analgesics, particularly in the treatment of chronic pain.

It is understood that, unless specified otherwise, the alkyl or acyl radicals or remainders are linear or branched and contain 1 to 7 carbon atoms, in particular the acyl radicals can be acetyl radicals. The aryl or aralkyl radicals can be mono or bicyclic radicals, comprising 6 to 10 members, for example phenyl, naphthyl, benzyl, phenethyl or naphthylalkyl. It is understood that the heterocyclyl radicals can be mono or bicyclic, aromatic or non-aromatic radicals comprising 5 to 10 members and containing 1 to 4 heteroatoms chosen from oxygen, nitrogen or sulphur. In particular they can be chosen from the thienyl, furyl, pyrrolyl, pyrrolidinyl piperidyl pyridyl, pyrazinyl, pyrimidinyl, pyridazinyl, piperazinyl, dioxolyl, imidazolyl, imidazolinyl, pyrazolyl, tetrazolyl, pyrannyl, tetrahydropyrannyl, tetrahydrofuranyl, oxazolyl, thiazolyl, thiazinyl, morpholinyl, thiomorpholinyl, indolyl, indolizinyl, quinolyl, naphthyridinyl radicals.

It is understood that the amino acids mentioned above can be in particular chosen from natural or non-natural amino acids, such as for example glycine, alanine, leucine, isoleucine, proline, valine, phenylalanine or H$_2$NC(CH$_3$)$_2$CO$_2$H, in L or D series and that these groups are protected prior to the synthesis reactions, in the form of amides or carbamates; the protection and release of the protective radicals is carried out according to the methods described by T. W. Greene and P. G. M. Wuts, Protective Groups in Organic Synthesis, 4th Edition ISBN 978-0-471-69754-1, December 2006. The halogen atoms are chosen from chlorine, fluorine, bromine and iodine. According to a preferred embodiment of the invention, the alkyl or acyl radicals are linear or branched and contain 1 to 4 carbon atoms.

According to the invention, the ester derivatives of 2-amino-2-phenyl-alkanol of general formula (I) are prepared by the action of a derivative of general formula:

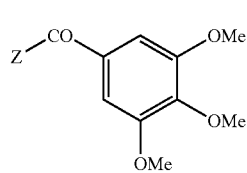

in which Z is a halogen atom, a hydroxy radical or the remainder of a reactive ester, on the derivative of 2-amino-2-phenyl alkanol, of general formula:

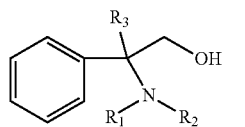

(III)

in which $R_1$ and $R_3$ are defined as previously and $R_2$ is defined as previously, followed if appropriate, when $R_2$ is the hydrogen atom, by substitution of the amine of the ester derivative of 2-amino-2-phenyl-alkanol obtained, of general formula:

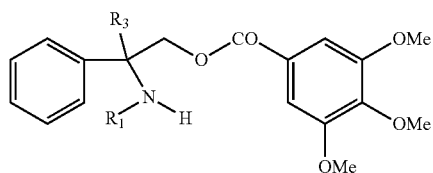

(IV)

in which $R_1$ and $R_3$ are defined as above,
either, when one wishes to obtain the derivatives for which $R_2$ is —CO—O—CHR$_4$—OCOR$_5$, by the action of the chloroalkylchloroformate, followed by the reaction of the product obtained with an alkaline salt of the corresponding acid $R_5$COOH, for example the sodium salt, the potassium salt or the caesium salt $R_5$COOCs, or also the silver salt or a quaternary ammonium salt (such as for example the tert-butyl ammonium salt), of this acid,
or, when one wishes to obtain derivatives for which $R_2$ is alkyl substituted, by acylation with an acid halide or a reactive ester of structure:

 $R_2$—CO—Z (V)

in which $R_2$ is defined as above and Z is a halogen atom or the remainder of a reactive ester, followed by the reduction of the amide formed to an amine.

The product of general formula (II) can be a reactive derivative of 3,4,5-trimethoxy benzoic acid such as an acid halide or a reactive ester. The reaction of the derivative of 2-amino-2-phenyl alkanol of general formula (III) is carried out preferably using a derivative for which $R_2$ is the hydrogen atom.

When the product of general formula (II) is a reactive derivative of 3,4,5-trimethoxy benzoic acid such as the acid halide or a reactive ester, the reaction of the derivative of general formula (II) on the derivative 2-amino-2-phenyl alkanol of general formula (III) is advantageously carried out in the presence of a nitrogenous base such as for example triethylamine, dimethylaminopyridine, diisopropylethylamine in the case of the acid halide of formula (II) and the reaction is generally carried out in an organic solvent such as a chlorinated solvent (dichloromethane, dichlorethane, chloroform for example), at a temperature comprised between 0 and 70° C., preferably operating under nitrogen. And in the case of a reactive ester of formula (II), in the presence of sodium methylate in an organic solvent such as toluene in the presence of an alcohol such as methanol or ethanol, at a temperature comprised between 25 and 150° C.

When Z is a halogen atom, it is advantageously chosen from chlorine or bromine. When the product of general formula (II) is 3,4,5-trimethoxy benzoic acid, the reaction is generally carried out in the presence of a carbodiimide, in a halogenated solvent (dichloromethane, dichlorethane, chloroform for example), at a temperature comprised between 0 and 70° C. It is understood that when one wishes to obtain a derivative of general formula (IV) in R or S form, a derivative of 2-amino-2-phenyl alkanol, of general formula (III) in R or S form is reacted. It is also understood that the derivatives of general formula (IV) in R or S form lead to the derivatives of general formula (I) in R or S form.

When one wishes to obtain a product for which the $R_2$ radical is —CO—O—CHR$_4$—OCOR$_5$, the operation is carried out by the action of chloroalkylchloroformate on the product of general formula (IV), the reaction is carried out in an organic solvent such as a chlorinated solvent (dichloromethane, dichlorethane for example), or such as an ether (tetrahydrofuran for example), at a temperature comprised between −10 and 50° C. It is followed by the reaction of the product obtained with an alkaline salt of the corresponding acid $R_5$COOH, for example the sodium salt, the potassium salt or the caesium salt, the silver salt, or a quaternary ammonium salt, in an organic solvent such as for example an amide such as dimethylformamide, a chlorinated solvent (dichloromethane for example), an ester (ethyl acetate for example), an aromatic hydrocarbon (toluene for example), a nitrile (acetonitrile for example), a ketone (acetone, methyl ethyl ketone for example), in the presence or in the absence of sodium iodide, at a temperature comprised between 0 and 60° C. By way of example, in the case where $R_1$ and $R_3$ form with the nitrogen atom a ring with 5 members and in the case where $R_2$ is —CO—O—C(CH$_3$)—O—CO—CH$_2$NHCOCH$_3$ the product can be prepared according to the following scheme:

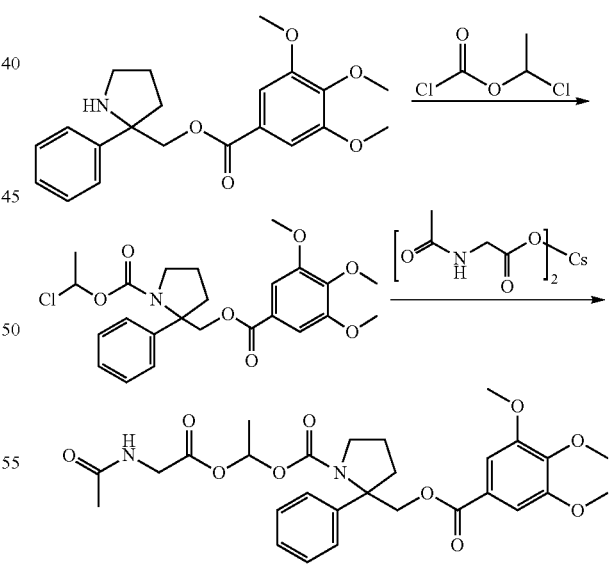

When one wishes to obtain a derivative of general formula (I) for which $R_2$ is a substituted alkyl, the acylation reaction of the amine of the derivative of general formula (IV) is carried out in a halogenated solvent (dichloromethane, dichlorethane for example) or in an ether (tetrahydrofuran), at a temperature comprised between 0 and 70° C. If appropriate the reactive ester can be prepared using hydroxybenzotriazole. The reduction is carried out in the presence of borane or aluminium and lithium hydride, in tetrahydrofuran, at a temperature comprised between 0 and 70° C.

The derivatives of 3,4,5-trimethoxy benzoic acid of general formula (II) can be prepared according to the usual methods for the conversion of carboxylic acids to their reactive derivatives, which does not alter the remainder of the molecule. The 2-phenyl-pyrrolidine-2-carboxylic acid, precursor of the alcohol of general formula (III), is a commercial product, its derivatives can be prepared by analogy with the synthesis of this product.

More particularly, the corresponding acids can be prepared according to and by analogy with the synthesis described by A. O. Martiryosyan, S. P. Gasparyan et al., Chemistry of Heterocyclic Compounds, vol. 36(4), 416-420 (2000), and particularly according to the following scheme:

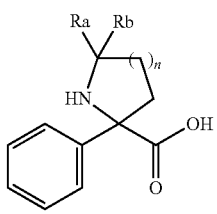

$n = 0, 1, 2, 3$ when $R_2$ is hydrogen, and $R_1$ and $R_3$ of formula (III) are represented in their cyclic form possibly having the substituents $R_a$ and $R_b$, or, when $R_2$ is other that the hydrogen atom, and $R_1$ and $R_3$ of formula (III) are represented in their cyclic form being able to bear the substituents $R_a$ and $R_b$ according to the diagram:

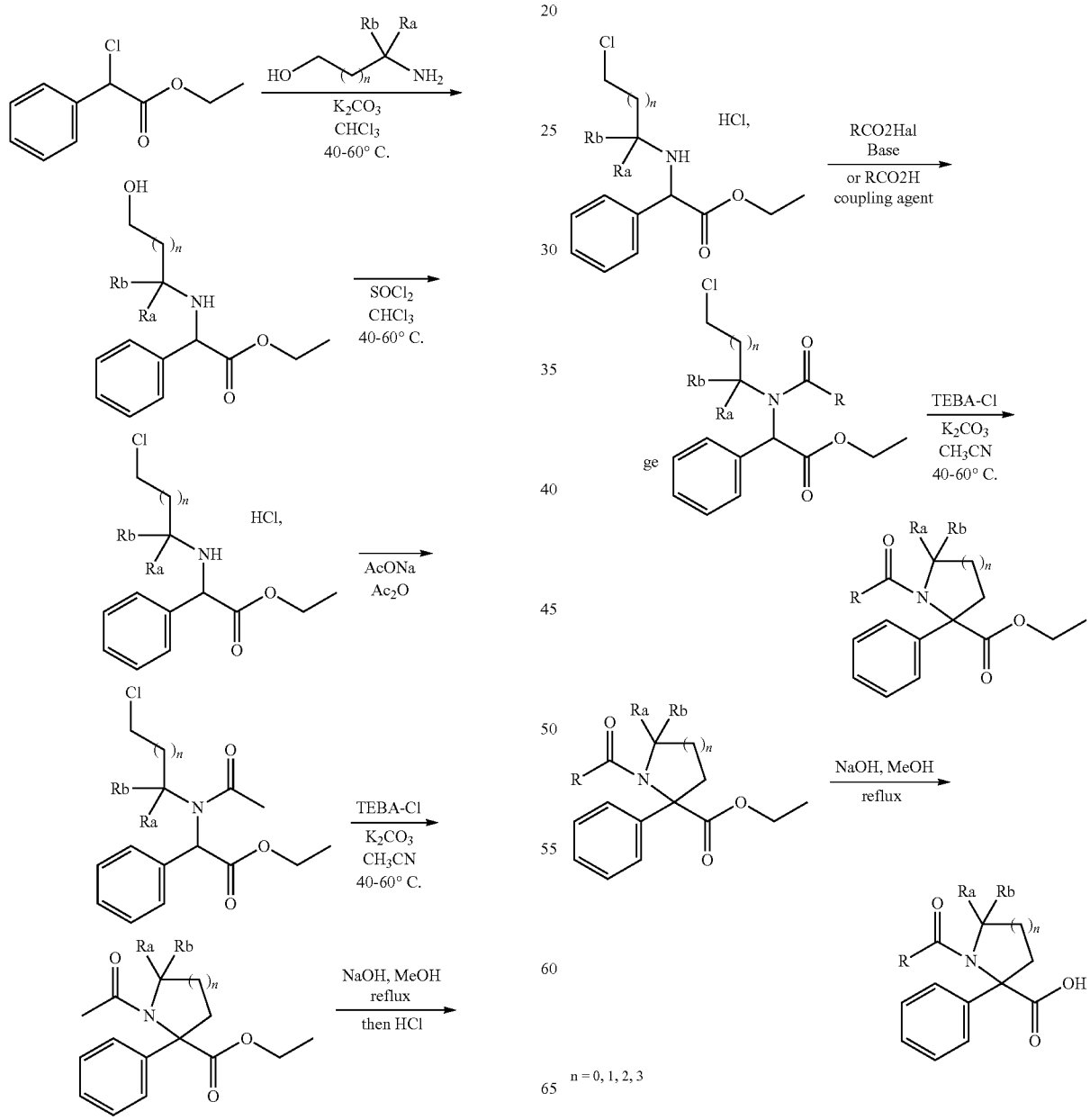

$n = 0, 1, 2, 3$

It being understood that the base used in the first stage can be a tertiary amine such as triethylamine or diisopropylethylamine and the coupling agent can be for example hydroxy benzotriazole.

Generally, the derivatives of general formula (III) can be prepared by reduction of the corresponding acid to alcohol, and by analogy with the method described in the patent applications FR 2 765 218 or EP 510 168. By way of example, according to the following scheme:

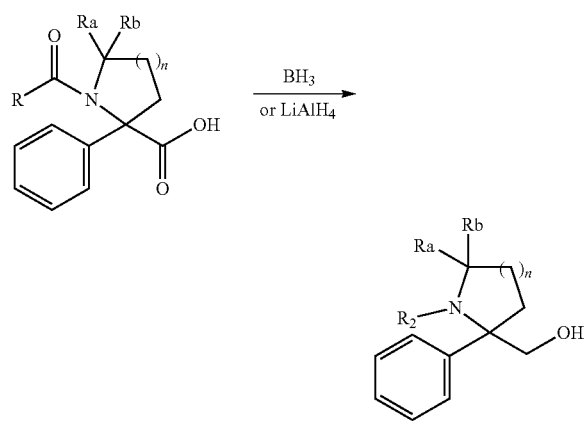

It is understood that when one intends to obtain a product of general formula (I) in the S or R form, a derivative of 2-amino-2-phenyl alkanol of general formula (III) in S or R form is reacted. The derivatives of 2-amino-2-phenyl alkanol of general formula (III) in S or R form can be prepared by separation according to the usual methods for separating enantiomers which do not affect the remainder of the molecule or by analogy with the method described in the European patent EP 510,168. When they exist the pharmaceutically acceptable salts can be addition salts with acids. In particular salts with the mineral acids such as for example the hydrochlorides, the hydrobromides, the sulphates, the phosphates or the addition salts with the organic acids such as for example the acetates, the maleates, the fumarates, the tartrates, the citrates.

The derivatives of general formula (I) can be purified according to the usual methods, in particular by chromatography or by crystallization. The derivatives of general formula (I) are particularly useful because of their powerful analgesic activity, in particular with regard to chronic pain.

Their activity has been demonstrated in vitro in the sodium channel inhibition test by application of the method of G. B. Brown, $^3$H-batrachotoxinin-A benzoate binding to voltage-sensitive sodium channels: inhibition by the channel blockers tetrodotoxin and saxitoxin, J. Neurosci., 6, 2064 (1986). In vitro in this test, the products according to the invention have exhibited activities between 25 and 90% inhibition for concentrations of 3.2 (μM). This activity is predictive of an antinociceptive effect and therefore with a potential efficacy for the treatment of visceral and neuropathic pain: Roman F. J. et al., J. Pharmacol. Exp. Ther., 289(3), 1391-97 (1999); V. Kayser et al., Life Sciences, 66(5), 433-39 (2000).

The important role of the sodium channels in nociception is widely supported by the literature: Wood J. N. et al., Voltage-gated sodium channels and pain pathways, J. Neurobiol., 61(1), 55-71 (2004); Cox J J. et al., Nature; 444 (7121), 894-8 (2006); Ahmad S. et al., Hum. Mol. Genet., 16(17), 2114-21 (2007). More particularly the therapeutic potential of the sodium channel inhibitors in the treatment of neuropathic pain is widely known: Devor M., Sodium channels and mechanisms of neuropathic pain., J. Pain., 7(1 Suppl 1), S3-S12 (2006). To date numerous synthesized products demonstrate that the sodium channel inhibitors can increase the benefit/risk profile of the therapeutic agents used in the treatment of pain: Veneroni et al., Pain., 102(1-2), 17-25 (2003); Ok et al., Bioorg. Med. Chem. Lett., 16(5), 1358-61 (2006); Ilyin et al., J. Pharmacol. Exp. Ther., 318(3), 1083-93 (2006); Jarvis et al., Proc. Natl. Acad. Sci. USA., 104 (20), 8520-5 (2007).

Moreover the products according to the invention do not exhibit known toxicity. Among the products of general formula (I), more particularly useful are the products for which: $R_1$ forms with $R_3$ and the nitrogen and carbon atoms to which they are respectively attached, a heterocycle with 4 to 7 members, optionally substituted in the α position of the nitrogen atom by one or two $R_a$ and $R_b$ radicals which can be independently of the other a hydrogen atom or a linear or branched alkyl and containing 1 to 4 carbon atoms, and $R_2$ is a hydrogen atom and among these products, in particular the ester derivatives of 2-amino-2-phenyl-alkanol of general formula (I) for which $R_1$ and $R_3$ form together with the nitrogen and carbon atoms to which they are respectively attached, a heterocycle with 4 to 7 members, and $R_2$ is a hydrogen atom, in their R or S forms or the mixtures thereof, as well as their pharmaceutically acceptable salts, if any.

More especially preferred are the products which are listed below:

3,4,5-trimethoxy-benzoic acid 2-phenyl-azetidin-2-yl methyl ester 3,4,5-trimethoxy-benzoic acid 4-methyl-2-phenyl-azetidin-2-yl methyl ester 3,4,5-trimethoxy-benzoic acid 4,4-dimethyl-2-phenyl-azetidin-2-yl methyl ester 3,4,5-trimethoxy-benzoic acid 2-phenyl-pyrrolidin-2-yl methyl ester 3,4,5-trimethoxy-benzoic acid 5-methyl-2-phenyl-pyrrolidin-2-yl methyl ester 3,4,5-trimethoxy-benzoic acid 5,5-dimethyl-2-phenyl-pyrrolidin-2-yl methyl ester 3,4,5-trimethoxy-benzoic acid 2-phenyl-piperidin-2-yl methyl ester 3,4,5-trimethoxy-benzoic acid 6-methyl-2-phenyl-piperidin-2-yl methyl ester 3,4,5-trimethoxy-benzoic acid 6,6-dimethyl-2-phenyl-piperidin-2-yl methyl ester 3,4,5-trimethoxy-benzoic acid 2-phenyl-azepan-2-yl methyl ester 3,4,5-trimethoxy-benzoic acid 7-methyl-2-phenyl-azepan-2-yl methyl ester 3,4,5-trimethoxy-benzoic acid 7,7-dimethyl-2-phenyl-azepan-2-yl methyl ester.

EXAMPLES

The following example illustrates the present invention. In the example which follows, the abbreviations used have the following meanings:

DMF dimethylformamide

DMSO dimethylsulphoxide

THF tetrahydrofuran

DIPEA N,N-diisopropylethylamine

TLC thin layer chromatography

Example 1

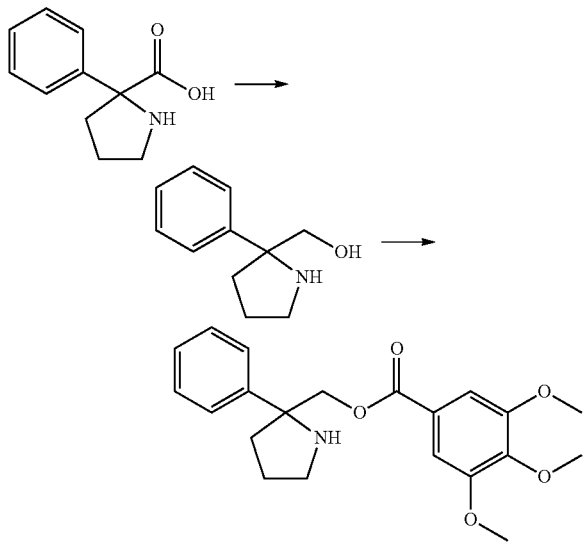

200 mg (0.001 mol) of (2-phenylpyrrolidin-2-yl)methanol are solubilized in 6 ml of toluene and 0.4 ml of methanol in a three-necked flask provided with a distillation bend. 0.026 g (0.00124) mol of 3,4,5-trimethoxy-benzoic acid methyl ester is added to the reaction mixture. The reaction mixture is heated to 130° C., then 61 mg (0.0011 mol) of sodium methoxide is added. The reaction mixture is left overnight at 130° C. and the methanol is distilled off. Another 0.0266 g of 3,4,5-trimethoxy-benzoic acid methyl ester is added and the reaction mixture is heated at 130° C. for 3 hours.

TLC on silica (CH2Cl2/MeOH: 95/5), indicates that the reaction is completed.

The reaction mixture is purified on a silica column: $CH_2Cl_2$/MeOH: 99/1 in order to produce 54 mg of the 2-phenyl-pyrrolidin-2-ylmethyl ester of 3,4,5-trimethoxybenzoic acid, in the form of a yellow oil (yield: 10%).

NMR 1H (300 MHz, CDCl3): δ (ppm)=1.56-2.17 (m, 4H, CH2); 2.96-3.15 (m, 2H, CH2N); 3.76-3.91 (3 (s), 9H, OCH3); 4.33 (dd, 2H, CH2O); 7.08 (s, 2H, ArH); 7.24-7.35 (m, 3H, ArH); 7.43-7.55 (d, 2H, ArH).

MS (ES+): [M+H]+, m/z: 372.2

2-phenylpyrrolidin-2-yl)methanol can be prepared in the following way:

2-phenyl-pyrrolidine-2-carboxylic acid (217.20 mg, 0.0011358 mol) is solubilized in tetrahydrofuran (THF) (5 mL) under a nitrogen atmosphere. 2.3 mL of a 1M solution of borane-THF complex, in solution in THF is added dropwise. The reaction mixture is heated to reflux for 3 hours then cooled down in an ice bath.

5 mL of a 5M solution of NaOH is added dropwise. The aqueous phase is extracted twice with 20 mL of methylene chloride. The resultant organic phase is dried over $Na_2SO_4$ then filtered and concentrated to dryness in a rotary evaporator. In this way, 200.0 mg of 2-phenylpyrrolidin-2-yl)methanol is obtained, in the form of a yellow oil (yield: 99%)

NMR 1H (300 MHz, CD3OD): δ (ppm)=1.64-2.17 (m, 4H, CH2); 2.80-3.08 (m, 2H, CH2N); 3.21 (m, 1H, NH); 3.42-3.58 (m, 2H, CH2O); 3.61 (m, 1H, OH); 7.08-7.43 (m, 5H, ArH).

The products of general formula (I) can be administered by oral, parenteral, perlingual or rectal route, in aerosols or in topical form. The present invention also relates to the pharmaceutical compositions comprising at least one ester derivative of 2-amino-2-phenyl-alkanol of general formula (I) and/or their salts, if any, in the pure state or in the form of a combination with one or more diluents or adjuvants which are compatible and pharmaceutically acceptable.

These compositions can be presented in the form of solid compositions, in particular in the form of tablets, coated tablets, pills, gelatin capsules, powders to be put in solution or in suspension, or granules, or in the form of liquid compositions such as injectable solutions or suspensions, drinkable solutions or suspensions, syrups, emulsions, elixirs containing inert diluents such as water or paraffin oil or in the form of suppositories, creams, ointments and lotions or also in the form of compositions to be sprayed. These pharmaceutical forms are prepared according to the usual methods.

In the solid compositions for oral administration the active ingredient according to the invention is mixed with one or more inert diluents or adjuvants, such as for example saccharose, lactose, starch or its derivatives, microcrystalline cellulose, colloidal silica, povidone, talc, gum arabic. These compositions can comprise substances other than diluents, for example a lubricant such as magnesium stearate or a coating intended for controlled release.

The liquid compositions for oral administration, can comprise aqueous or non aqueous vehicles such as diluents and can also comprise other substances such as for example wetting, sweetening or flavouring products. The non aqueous compositions can comprise fatty substances of animal or vegetable origin, paraffin derivatives, glycols, soya lecithin.

The compositions which can be administered by parenteral route are more particularly compositions which can be administered by intramuscular or intravenous route. The compositions for parenteral administration, can be sterile solutions or emulsions. The following can be used as solvent or vehicle: propylene glycol, polyethylene glycol, vegetable oils, in particular olive oil, injectable organic esters, for example ethyl oleate. These compositions can also contain adjuvants, in particular wetting, isotonizing, emulsifying, dispersing, stabilizing agents, and/or preservatives.

The sterilization can be carried out in several ways, for example using a bacteriological filter, by irradiation or by heating. The compositions can also be prepared in the form of sterile solid compositions which are dissolved at the time of use in sterile water or any other injectable sterile medium.

The compositions for rectal administration are suppositories or rectal capsules, which contain in addition to the active ingredient, excipients such cocoa butter, semi-synthetic glycerides or polyethylene glycols. The compositions for topical administration can be for example patches which contain, in addition to the active ingredient, compatible excipients such as silicone oil, paraffin.

The compositions can also be aerosols. For use in the form of liquid aerosols, the compositions can be stable sterile solutions or solid compositions dissolved at the time of use in apyrogenic sterile water, in serum or any other pharmaceutically acceptable vehicle. For use in the form of dry aerosols intended to be inhaled directly, the active ingredient is finely divided and combined with a diluent or water-soluble solid vehicle with a granulometry of 30 to 80 μm, for example dextran, mannitol or lactose.

In human therapeutics, the doctor will determine the dosage that he estimates to be the most appropriate for treatment, depending on the age, the weight, and other factors appropriate to the patient to be treated. The usual dose, which can vary according to the patient to be treated and the disease in question, can be, for example, from 50 mg to 2 g per day for an adult, by oral route.

The following example illustrates a composition according to the invention.

Example 2

A formulation which can be administered by oral route is prepared, with the following composition:
2-phenyl-pyrrolidin-2-ylmethyl ester of 3,4,5-trimethoxy-benzoic acid . . . 100 mg
lactose monohydrate,
modified corn starch,
hydroxypropyl methylcellulose,
sodium carboxymethyl starch,
tartaric acid,
colloidal silica,
magnesium stearate,
macrogol 4000,
titanium dioxide.

The invention claimed is:

1. A compound of formula (I):

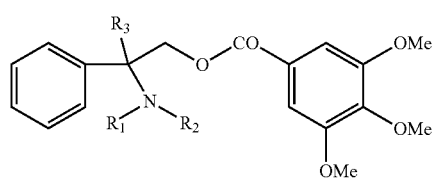

in which:
R$_1$ forms with R$_3$ and the nitrogen and carbon atoms to which they are respectively attached, a heterocycle with 4 to 7 members, the heterocycle being optionally substituted in the α position of the nitrogen atom by one or two R$_a$ and R$_b$ radicals which can be independently of the other a hydrogen atom or a linear or branched alkyl containing 1 to 4 carbon atoms; and R$_2$ is a hydrogen atom or represents a —CO—O—CHR$_4$—OCOR$_5$ radical for which R$_4$ is a hydrogen atom or a linear or branched alkyl radical containing 1 to 4 carbon atoms, and R$_5$ is an alkyl radical, or R$_2$ represents an alkyl radical in a linear or branched chain containing 1 to 4 carbon atoms, or a linear or branched alkyl radical containing 2 to 4 carbon atoms substituted by hydroxy, alkoxy, alkylthio, amino, alkylamino, or dialkylamino, wherein the alkyl parts of the dialylamino can form with the nitrogen atom to which they are attached, a heterocycle with 5 or 6 members, the substituted 2 to 4C alkyl radical comprising at least 2 carbon atoms between the nitrogen atom bearing R$_2$ and the substituent;

the alkyl radicals being, unless specified otherwise, linear or branched and containing 1 to 7 carbon atoms;

in its R or S forms or their mixtures, as well as its pharmaceutically acceptable salts, if any.

2. The compound according to claim 1, wherein R$_1$ and R$_3$ form together with the nitrogen and carbon atoms to which they are respectively attached, a heterocycle with 4 to 7 members, and R$_2$ is a hydrogen atom, in its R or S forms or their mixtures, as well as its pharmaceutically acceptable salts, if any.

3. The compound according to claim 1, wherein it corresponds to one of the following structures:

3,4,5-trimethoxy-benzoic acid 2-phenyl-azetidin-2-yl methyl ester;

3,4,5-trimethoxy-benzoic acid 4-methyl-2-phenyl-azetidin-2-yl methyl ester;

3,4,5-trimethoxy-benzoic acid 4,4-dimethyl-2-phenyl-azetidin-2-yl methyl ester;

3,4,5-trimethoxy-benzoic acid 2-phenyl-pyrrolidin-2-yl methyl ester;

3,4,5-trimethoxy-benzoic acid 5-methyl-2-phenyl-pyrrolidin-2-yl methyl ester;

3,4,5-trimethoxy-benzoic acid 5,5-dimethyl-2-phenyl-pyrrolidin-2-yl methyl ester;

3,4,5-trimethoxy-benzoic acid 2-phenyl-piperidin-2-yl methyl ester;

3,4,5-trimethoxy-benzoic acid 6-methyl-2-phenyl-piperidin-2-yl methyl ester;

3,4,5-trimethoxy-benzoic acid 6,6-dimethyl-2-phenyl-piperidin-2-yl methyl ester;

3,4,5-trimethoxy-benzoic acid 2-phenyl-azepan-2-yl methyl ester;

3,4,5-trimethoxy-benzoic acid 7-methyl-2-phenyl-azepan-2-yl methyl ester; or 3,4,5-trimethoxy-benzoic acid 7,7-dimethyl-2-phenyl-azepan-2-yl methyl ester.

4. A process for preparing a compound of claim 1, wherein a compound represented by formula (II):

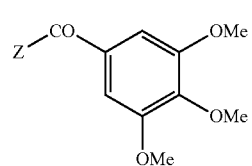

in which Z is a halogen atom, a hydroxy radical or the remainder of a reactive ester, is reacted on the compound represented by formula (III):

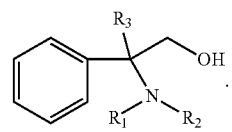

5. A pharmaceutical composition comprising a compound of claim 1 in the pure state or in the form of a combination with one or more compatible and pharmaceutically acceptable diluents or adjuvants.

6. The method according to claim 4 further comprising, when R2 is —CO—O—CHR$_4$—OCOR$_5$, reacting the compound of formula (IV)
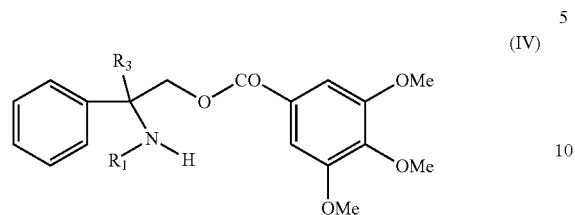
(IV)
with chloroalkylchloroformate, and further reacting with an alkaline salt, a silver salt, or a quaternary ammonium salt of the corresponding acid R$_5$COOH.
* * * * *

UNITED STATES PATENT AND TRADEMARK OFFICE
CERTIFICATE OF CORRECTION

PATENT NO. : 8,436,192 B2  
APPLICATION NO. : 13/387462  
DATED : May 7, 2013  
INVENTOR(S) : Pachot et al.

Page 1 of 1

It is certified that error appears in the above-identified patent and that said Letters Patent is hereby corrected as shown below:

On the title page, item [73]: "Oraxcell" - should be - Oroxcell

Signed and Sealed this  
Tenth Day of September, 2013

Teresa Stanek Rea  
*Acting Director of the United States Patent and Trademark Office*